(12) United States Patent
Swoyer et al.

(10) Patent No.: US 6,952,613 B2
(45) Date of Patent: Oct. 4, 2005

(54) IMPLANTABLE GASTROINTESTINAL LEAD WITH ACTIVE FIXATION

(75) Inventors: John M Swoyer, Andover, MN (US); Warren Starkebaum, Plymouth, MN (US); Martin T. Gerber, Maple Grove, MN (US); Tim Herbert, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 473 days.

(21) Appl. No.: 10/045,701

(22) Filed: Jan. 11, 2002

(65) Prior Publication Data

US 2002/0103521 A1 Aug. 1, 2002

Related U.S. Application Data

(60) Provisional application No. 60/265,369, filed on Jan. 31, 2001, provisional application No. 60/265,503, filed on Jan. 31, 2001, and provisional application No. 60/265,505, filed on Jan. 31, 2001.

(51) Int. Cl.$^7$ .............................. A61N 1/18; A61N 1/05
(52) U.S. Cl. .......................................... 607/40; 607/133
(58) Field of Search ................................ 607/133, 126, 607/40, 41, 74, 116, 127, 128, 118; 600/325, 486

(56) References Cited

U.S. PATENT DOCUMENTS

| | | | |
|---|---|---|---|
| 3,333,045 A | 7/1967 | Fisher et al. | |
| 3,472,234 A | 10/1969 | Tachick | |
| 3,737,579 A | 6/1973 | Bolduc | |
| 3,866,615 A | 2/1975 | Hewson | |
| 4,000,745 A | 1/1977 | Goldberg | |
| 4,010,758 A | 3/1977 | Rockland et al. | |
| 4,177,818 A | 12/1979 | De Pedro | |
| 4,235,246 A | 11/1980 | Weiss | |
| 4,313,448 A | 2/1982 | Stokes | |
| 4,357,946 A | 11/1982 | Dutcher | |
| 4,424,818 A | 1/1984 | Doring | |
| 4,452,254 A | 6/1984 | Goldberg et al. | |
| 5,085,218 A | * 2/1992 | Heil et al. | 600/373 |
| 5,143,090 A | * 9/1992 | Dutcher et al. | 607/121 |
| 5,328,442 A | 7/1994 | Levine | |
| 5,423,872 A | 6/1995 | Cigaina | |
| 5,425,751 A | 6/1995 | Baeten et al. | 607/28 |
| 5,489,294 A | 2/1996 | McVenes et al. | 607/120 |
| 5,507,289 A | 4/1996 | Essen-Moller | |
| 5,690,691 A | 11/1997 | Chen et al. | |
| 5,716,392 A | 2/1998 | Bourgeois et al. | 607/132 |
| 5,836,994 A | * 11/1998 | Bourgeois | 607/40 |
| 5,837,006 A | 11/1998 | Ocel et al. | 607/127 |
| 5,861,014 A | 1/1999 | Familoni | 607/40 |
| 6,026,326 A | 2/2000 | Bardy | |
| 6,104,965 A | 8/2000 | Lim | |
| 6,216,039 B1 | 4/2001 | Bourgeois | |
| 6,243,607 B1 | 6/2001 | Mintchev et al. | |

FOREIGN PATENT DOCUMENTS

GB   1277107   6/1972

* cited by examiner

Primary Examiner—Jeffrey R. Jastrzab
(74) Attorney, Agent, or Firm—Thomas F. Woods

(57) ABSTRACT

Active fixation, gastrointestinal leads adapted to be implanted within the body at a site of the GI tract to conduct electrical stimulation from an implantable or external gastrointestinal stimulator to the site and to conduct electrical signals of the GI tract from the site to the implantable or external gastrointestinal stimulator are disclosed. Disclosed active fixation mechanisms include one or more of hooks, and helixes extending from stops, e.g. plates, of an electrode head and functioning as stimulation/sense electrodes in unipolar and bipolar configurations or simply as fixation mechanisms. The active fixation mechanisms are coated to reduce inflammation and polarization effects.

9 Claims, 12 Drawing Sheets

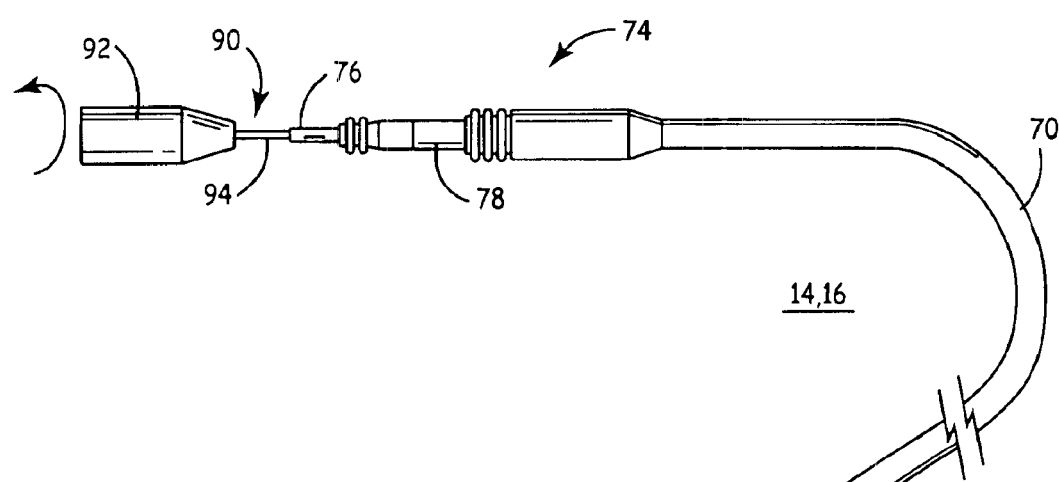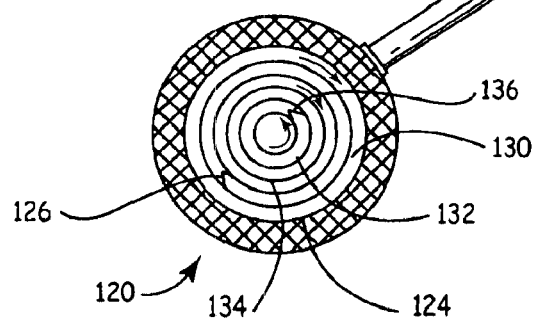
FIG. 9

IMPLANTABLE GASTROINTESTINAL LEAD WITH ACTIVE FIXATION

RELATED APPLICATIONS

This application claims priority to provisional U.S. Application Ser. No. 60/265,369, filed Jan. 31, 2001, provisional U.S. Application Ser. No. 60/265,503, filed Jan. 31, 2001, and provisional U.S. Application Ser. No. 60/265,505, filed Jan. 31, 2001.

This disclosure is related to the following co-pending application entitled IMPLANTABLE BIFURCATED GASTROINTESTINAL LEAD WITH ACTIVE FIXATION by Swoyer et al (Application No. (P-9868.00); filed Jan. 11, 2002), which is not admitted as prior art with respect to the present disclosure by its mention in this section.

FIELD OF THE INVENTION

The present invention pertains to gastrointestinal leads adapted to be implanted within the body with one or more than one stimulation/sense electrode affixed at a site of the gastrointestinal tract (GI tract) to conduct electrical stimulation from an implantable or external electrical neurostimulator to the site and to conduct electrical signals of the GI tract from the site to the implantable or external electrical neurostimulator, and particularly to unipolar and bipolar gastrointestinal leads having an active fixation mechanism that attaches the stimulation/sense electrode(s) at the site that may comprise an electrode.

BACKGROUND OF THE INVENTION

The GI tract comprises the esophagus, the stomach, the small intestine, the large intestine, the colon, and the anal sphincter and is generally described as having a tract axis. Like other organs of the body, most notably the heart, these organs naturally undergo regular rhythmic contractions. In particular these contractions take the form of peristaltic contractions and are essential for the movement of food through each of the respective organs. Like the heart, these contractions are the result of regular rhythmic electrical depolarizations of the underlying tissue. With regards to the small intestine and large intestine, normal electrical depolarizations ("slow waves") typically occur at a rate of approximately 15 and 1 beats per minute (bpm) respectively. Similarly, in the stomach, normal slow waves typically occur at a rate approximately 3 bpm. Not all of these depolarizations, however, normally result in a contraction of the organ. Rather contractions occur upon the occurrence of a normal electrical depolarizations followed by a series of high frequency spike activity.

In some individuals, however, either the regular rhythmic peristaltic contractions do not occur or the regular rhythmic electrical depolarizations do not occur or both do not occur. In each of these situations the movement of food may be seriously inhibited or even disabled. Such a condition is often called "gastroparesis" when it occurs in the stomach. Gastroparesis is a chronic gastric motility disorder in which there is delayed gastric emptying of solids or liquids or both. Symptoms of gastroparesis may range from early satiety and nausea in mild cases to chronic vomiting, dehydration, and nutritional compromise in severe cases. Similar motility disorders occur in the other organs of the GI tract, although by different names.

Diagnosis of gastroparesis is based on-demonstration of delayed gastric emptying of a radio-labeled solid meal in the absence of mechanical obstruction. Gastroparesis may occur for a number of reasons. Approximately one third of patients with gastroparesis, however, have no identifiable underlying cause (often called idiopathic gastroparesis). Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the GI tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

For many years, sensing of the peristaltic electrical wave and gastrointestinal stimulation at various sites on or in the GI tract wall of the digestive system or nerves associated therewith have been conducted to diagnose and treat these various conditions. The history and breadth of such sensing and GI tract stimulation is set forth in commonly assigned U.S. Pat. Nos. 5,507,289, 6,026,326, 6,104,965, 6,216,039, and in further U.S. Pat. Nos. 5,690,691 and 6,243,607, for example.

Electrical stimuli are applied from the neurostimulator implantable pulse generator (IPG) through leads and electrodes affixed at sites in the body of the patient or the GI tract wall that permit the electrical stimulus to produce a local contraction of a desired portion of the GI tract. The sites of the GI tract wall comprise the outermost serosa or sub-serosally in the inner, circumferential and longitudinal (and oblique in the case of the stomach) smooth muscle layers referred to as the "muscularis externa". The smooth muscle is preferably comprised of innervated muscle tissue, and it is theorized that the smooth muscle is neurally electrically stimulated through the nerves associated with and innervating the muscle tissue in order to produce the contraction of the smooth muscle.

An implantable method and system for electrical stimulation of smooth muscle with intact local gastric nerves comprising a portion of the GI tract is disclosed in the above-referenced '607 patent. The electrical stimulation of the smooth muscle effects local contractions at sites of a portion of the GI tract that are artificially propagated distally therethrough in order to facilitate or aid at least a partial emptying of such portion. This stimulation attempts to create a simulated system that reproduces the spatial and temporal organization of normal gastric electrical activity by creating and controlling local circumferential non-propagated contractions. In this simulated gastric pacing system, each local circumferential contraction is invoked by applying an electrical stimulus to the smooth muscle circumferentially about the portion of the GI tract in a plane substantially perpendicular to the longitudinal axis of the portion. The electrical stimulus is applied at a proximal location and at at least one distal location. The distal location is in axially spaced relationship relative to the proximal location. Further, the applied electrical stimulus is selected to be sufficient to stimulate the smooth muscle to produce the local circumferential contractions at the proximal and distal locations.

The Medtronic® Itrel III® Model 7425 IPG and pairs of the unipolar Model 4300 or Model 4301 or Model 4351 "single pass" leads available from MEDTRONIC, INC. have been implanted to provide stimulation to sites in the stomach wall to treat chronic nausea and vomiting associated with gastroparesis. The unipolar electrode of these leads comprises a length of exposed lead conductor and is of the type disclosed in commonly assigned U.S. Pat. Nos. 5,425, 751, 5,716,392 and 5,861,014. The above-referenced '039 patent and the '014 patent disclose the Model 4300 lead sewn through the serosa laterally into the muscularis externa to dispose the stimulation/sense electrode therein. A large incision is necessary to access the site, and a needle is used to perforate the serosa and muscularis externa laterally without fully penetrating the wall and to draw the stimulation/sense electrode into the muscularis externa. A laparascopic approach can be taken, but it is difficult to maneuver the needle to effect the fixation of the stimulation/sense electrode at the site. It is suggested in the '039 patent that two or more electrodes of this type can be formed along the length of the lead body that would be sewn laterally through and disposed within the muscularis externa.

The stimulation/sense electrodes conventionally employed in such gastrointestinal stimulation systems are formed of bio-compatible material shaped to either bear against the serosa or penetrate sub-serosally into the muscularis externa and polished to present an impervious outer surface. It is also suggested in the above-referenced '014 patent that the exposed electrode(s) of the single pass lead can alternatively be formed of other biocompatible electrode materials, including porous, platinized structures and could feature various pharmaceutical agents. Suggested pharmaceutical agents include dexamethasone sodium phosphate or beclomethasone phosphate in order to minimize the inflammatory response of the tissue to the implanted lead.

The above-referenced, commonly assigned, '326 patent shows a pin electrode mounted to extend orthogonally from a planar surface of a plate, wherein the pin electrode has a sharpened tip and is pressed through the serosa. The plate abuts against the serosa to limit the depth of penetration of the pin electrode to its length and has suture holes through it enabling the plate to be sutured to the GI tract wall to prevent dislodgement.

A further gastrointestinal lead bearing a pin electrode extending axially from the distal end of the lead body is disclosed in U.S. Pat. No. 5,423,872. In one version, the pin electrode is formed with distal tip retention barbs 21 that are pressed into the gastrointestinal wall and maintained in position by a suture passed through a suture pad. In a further version, more distally disposed and retractable barbs 37 are deployed to stabilize the pin electrode. In this variation, the lead body is formed with coaxial conductors to provide a bipolar lead, whereby a ring-shaped electrode 33 surrounds the distally and axially extending, pin electrode 31.

Thus, certain of the stimulation/sense electrodes that have been employed or disclosed in the above-referenced gastrointestinal stimulation systems are affixed in place by sutures, requiring surgical exposure of the GI tract wall at the site sufficient to enable suturing. In the case of the lead disclosed in the '872 patent, prevention of axial movement and perforation of the GI tract wall at the site of attachment cannot be assured by the limited engagement of the necessarily short and minute fixation barbs with the serosa or sub-serosa tissue. More robust fixation mechanisms are needed to avoid migration of the stimulation/sense electrode resulting either in dislodgement or perforation of the GI tract wall.

In the field of cardiac stimulation, cardiac pacing leads having bipolar and unipolar pace/sense electrodes have long been used in conjunction with pacing system IPGs to conduct pacing pulses generated by the IPG to a site of the heart and cardiac signals from the site to the IPG. Pacing leads are typically provided with a passive fixation or an active fixation mechanism at the lead body distal end that is passively or actively engaged with cardiac tissue to anchor a distal tip electrode at a desired site in or on the heart. Passive fixation generally involves an atraumatic fixation lodging the distal electrode against the endocardium or within a coronary blood vessel. Positive or active fixation generally involves a more traumatic penetration of a fixation mechanism into the myocardium from an endocardial or epicardial surface, and the active fixation mechanism commonly comprises a distal pace/sense electrode. Typically, the active fixation mechanism comprises the single pace/sense electrode or one of the bipolar pace/sense electrodes, but can be separate and electrically isolated from the pace/sense electrodes.

Endocardial pacing leads having either active fixation or passive fixation mechanisms are implanted by a transvenous route into a heart chamber to locate the distal pace/sense electrode(s) at a selected site in the heart chamber where an active or passive fixation mechanism is deployed to maintain the pace/sense electrode affixed at the site. Endocardial active fixation pacing leads typically employ extendable and retractable helixes of hooks that are retracted during introduction and are extended distally from the lead body distal end at the site of attachment as shown, for example, in commonly assigned U.S. Pat. No. 5,837,006.

Epicardial pacing leads are implanted by exposure of the epicardium of the heart through a limited thoracotomy. The distal end of the epicardial lead formed with one or two pace/sense electrodes and an active fixation mechanism supported by an electrode head is affixed through the epicardium and within the myocardium. Active fixation mechanisms of epicardial pacing leads typically comprise a tissue penetrating, self-affixing mechanism extending away from a support or base or plate of the electrode head. The fixation mechanism is forced into the myocardium typically employing an insertion tool engaging the electrode head until it is fully seated within the myocardium and the plate bears against the epicardium. The plate is typically formed with a tissue ingrowth encouraging fabric or lattice, whereby tissue ingrowth about the plate assists in chronic anchoring to the heart.

One such active fixation, unipolar, epicardial pacing lead comprises the Medtronic® Model 6917 lead disclosed in commonly assigned U.S. Pat. No. 3,737,579. The active fixation mechanism comprises a rigid helix having a sharpened tip that is coupled with a lead conductor within the electrode head and a helix axis. The helix is mounted to the electrode head such that the helix axis extends orthogonally to the plate. The distal electrode comprises an uninsulated portion of the helix. A bipolar version of leads of this type is disclosed in commonly assigned U.S. Pat. No. 4,010,758 wherein an annular or ring-shaped electrode is formed on the plate surface around the helix and coupled to a second lead conductor within the electrode head. Other variations of such epicardial screw-in leads include multiple co-axial and intertwined helixes or a helix axially surrounding a pin extending coaxially with the helix axis from the electrode head, e.g., those shown in U.S. Pat. Nos. 4,235,246 and 4,452,254 and in UK Patent No. 1,277,107.

During implantation, the lead body and electrode head are mounted to an elongated tool, and the sharpened tip of the helix is advanced through the incision to perforate the epicardium. The tool and lead are rotated to screw the helix in until the plate abuts the epicardium, and the electrode head is detached from the tool.

The U.K. '107 patent discloses a unipolar epicardial lead having a single helically-shaped fixation mechanism and a bipolar lead having two, intertwined, helically-shaped fixation mechanisms mounted to an electrode head and a tool for rotating the electrode head to screw the fixation mechanism(s) into the myocardium. Each helically-shaped fixation mechanism comprises and insulated wire coil fixed at one end to the electrode head and terminating at an exposed sharpened tip that perforates the epicardium and acts as a pace/sense electrode embedded within the myocardium. In the bipolar embodiment, the sharpened tips are displaced diametrically from one another across the common coil diameter, and pacing and near-field sensing take place between the closely spaced sharpened tip electrodes.

The '246 patent discloses a bipolar epicardial lead having a single helically-shaped fixation mechanism and a straight pin electrode mounted to an electrode head, both having sharpened tips, and a tool for rotating the electrode head to screw the helically-shaped fixation mechanism and drive the straight pin electrode into the myocardium. The exposed sharpened tips that perforate the epicardium act as pace/sense electrodes embedded within the myocardium. The sharpened tips are displaced from one another, and pacing and near-field sensing take place between the closely spaced sharpened tip electrodes.

The '254 patent discloses a myocardial screw-in lead adapted to be screwed into the myocardium of the atrial wall having a shorter helix length than the helix length of such myocardial screw-in leads intended to be screwed into the ventricular myocardium through the epicardium. Additional hooks surround the helical electrode to catch in the epicardium and augment the fixation.

A further epicardial screw-in lead is disclosed in commonly assigned U.S. Pat. No. 4,357,946 wherein the helix is mounted to a gear mechanism within the electrode head. The helix can itself be rotated to screw into the myocardium without rotating or moving the electrode head by a rotation of a removable stylet extending through the length of the lead body and engaging the gear mechanism. Both unipolar and bipolar embodiments are disclosed.

A further active fixation, unipolar, epicardial lead comprises the Medtronic® Model 6951 lead disclosed in commonly assigned U.S. Pat. No. 4,313,448. The active fixation mechanism comprises forward facing barbed electrode having the tip at a predetermined angle with relation to the shank of the stimulation/sense electrode and with respect to a flexible base pad or plate of the electrode head. The plate has a substantially centered hole and a plurality of outer holes for fibrous ingrowth, and the shank of the stimulation/sense electrode extends out through the substantially centered hole. The barbed electrode is pushed into the myocardial tissue to the point where the base pad engages against the epicardium thereby indicating full implantation within the myocardium. During implantation, a stiffening stylet is employed to stiffen the lead body and a forceps is employed to grasp the electrode head to push the barb into the myocardium. A still further cardiac lead employing multiple hooks and a fixation tool for retracting the hooks during implantation is disclosed in U.S. Pat. No. 4,177,818.

Such active fixation, unipolar and bipolar cardiac pacing leads have not, to our knowledge, been employed in the field of gastrointestinal stimulation. The myocardium is formed of muscle layers that are typically thicker and stiffer when pressed against than the muscle layers of the organ walls of the GI tract. The organ walls of the GI tract, e.g. the stomach wall, are thinner and more compliant and less massive than the heart wall, so they are difficult to prevent from simply collapsing when pressed against. The serosa is not a tough membrane that an electrode can catch in like the epicardium. Also, the overall mass of the heart is much greater than the stomach. For these reasons, it can be difficult to get anything like a hook or screw-in helix to penetrate the outer serosa of the GI tract, not perforate all the way through the GI tract wall and to stay affixed chronically.

SUMMARY OF THE INVENTION

The present invention is preferably embodied in a GI tract lead adapted to be implanted within the body at a site of the GI tract to conduct electrical stimulation from an implantable or external neurostimulator to the site and to conduct electrical signals of the GI tract from the site to the implantable or external neurostimulator IPG.

The active fixation mechanisms preferably extend away from a stop or plate of the electrode head and are shaped to penetrate through the serosa and into the muscularis externa upon application of penetrating force through the electrode head to the GI tract wall to draw the stop or plate against the serosa and operatively contact the stimulation/sense electrode with the GI tract wall. The stop or plate inhibits further advancement of the active fixation mechanism and perforation of the GI tract wall, and the active fixation mechanism cooperates with the stop or plate to inhibit dislodgement of the stimulation/sense electrode from operative contact with the GI tract wall.

The active fixation mechanisms are selected from helixes and barbed hooks having sharpened tips or free ends that perforate the serosa and lodge in the muscularis externa or the submucosa. The maximal depth of penetration from the stop or plate is preferably in the range of 1 mm to 15 mm when the site comprises the antrum or in the range of 1 mm to 10 mm when the site comprises corpus or fundus to ensure that the free end does not extend substantially through the stomach wall.

The helixes and hooks can be formed of bio-compatible conductive materials that are coupled with the lead conductors and un-insulated at least in part to operate as the sensing and/or stimulation electrodes. The stimulation/sense electrode surface can be coated with a porous platinized structure to reduce polarization and/or an anti-inflammatory agent that inhibits inflammation that can negatively affect the ability to sense electrical signals of the GI tract or to efficiently deliver electrical stimulation. The anti-inflammatory agents can be embedded into a monolithic controlled release device (MCRD) carried by the electrode head.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 9 is a further view of the unipolar or bipolar, dual helix screw-in lead of the type depicted in FIG. 7;

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. In accordance with an aspect of the present invention, improved GI tract stimulation and sensing leads and methods and systems for effecting sensing and stimulation of at least one organ or region of the GI tract are provided.

Figure 1:
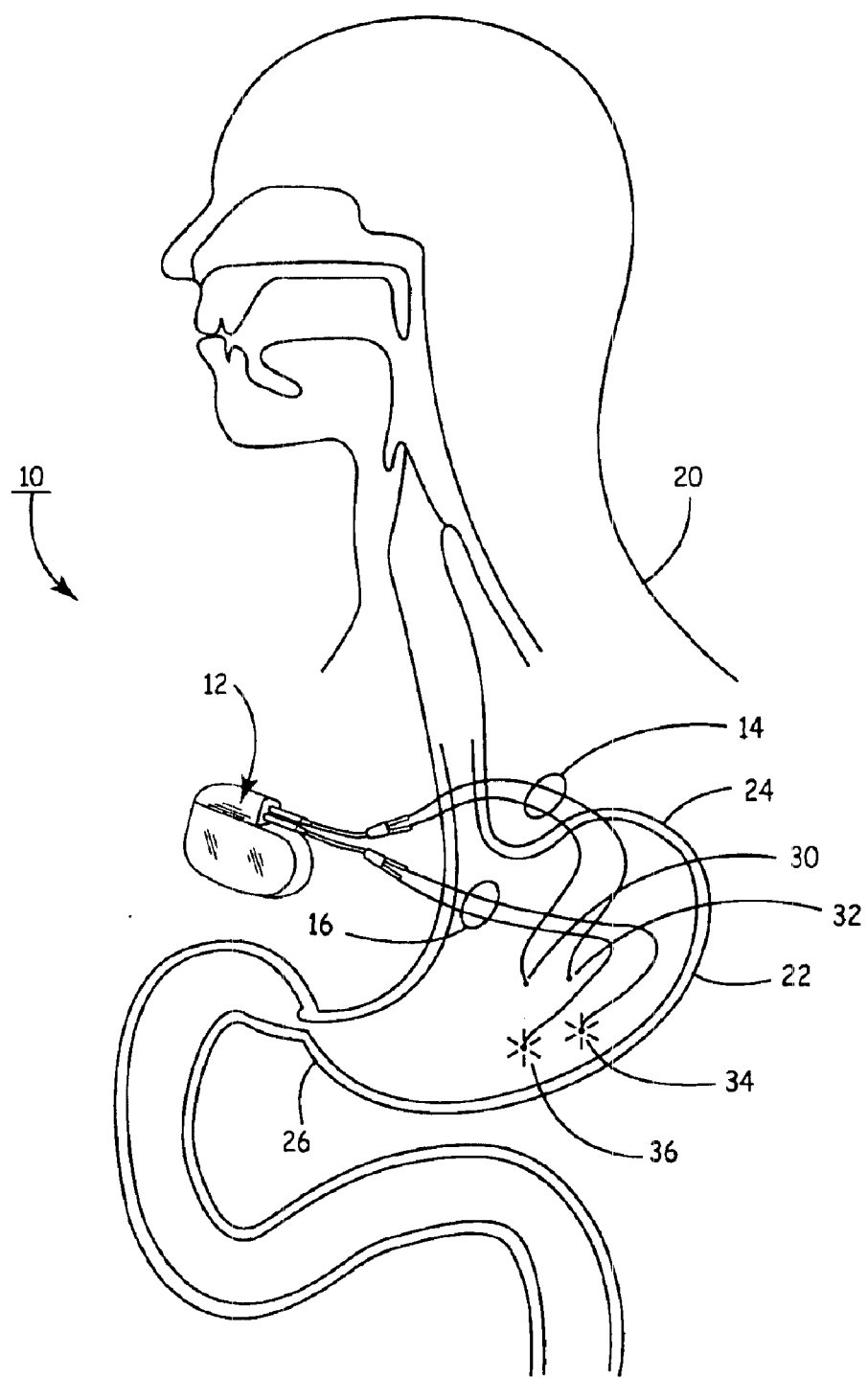
FIG. 1 is a schematic view of one example of the implantation of a GI tract IPG and lead system for sensing and delivering stimulation pulses to the stomach.

A GI tract stimulation system 10 known in the prior art from the above-referenced '955 patent, for example, comprises an IPG 12 having a plurality of leads extending to sensing and/or stimulation electrodes passed through the serosa and embedded into the GI tract wall, e.g., the muscularis externa of the stomach wall, and held there by sutures. The stimulation/sense electrodes of the GI tract leads are shown in FIG. 1 coupled to the stomach wall through use of the fixation mechanisms of the present invention. However, it will be understood that the GI tract lead electrodes may be affixed along or to any of the other structures and organ walls along the GI tract, including the colon, small intestine, stomach, or even the esophagus.

The gastric stimulation/sense leads of the present invention that are attached to such an IPG 12 employ active fixation mechanisms and insertion tools that grip the leads during implantation to embed the stimulation/sense electrodes of the leads through the serosa and into the muscularis externa and thereby stabilize the stimulation/sense leads. Once the attachment of the stimulation/sense electrodes is made, the lead connector elements at the lead body proximal ends are attached to the IPG 12.

For example, FIG. 1 illustrates either two bipolar leads (or two pairs of unipolar leads) 14 and 16 implanted in a patient 20. In either case, the GI tract leads 14 or 16 of the present invention that are attached to such an IPG 12 employ active fixation mechanisms. Insertion tools are employed during implantation that grip the electrode heads or fixation mechanism and, in certain cases, the lead body, to embed the fixation mechanism of each electrode head through the serosa and substantially into the muscularis externa and thereby stabilize the stimulation/sense electrodes. The stimulation/sense electrodes can comprise the fixation mechanism or be separated from the fixation mechanism. The lead connector assembly at each lead body proximal ends is inserted into an IPG connector socket of the IPG 12 once the fixation is accomplished. The stimulation/sense electrodes of the GI tract leads 14 and 16 are shown in FIG. 1 coupled to the stomach wall through use of the positive or active fixation mechanisms of the present invention.

For example, the first GI tract lead 14 extends to stimulation/sense electrodes 30 and 32 implanted against the serosa of stomach wall 24 in a first pair of locations, and the second GI tract lead 16 extends to stimulation/sense electrodes 34 and 36 implanted against the serosa of stomach wall 24 in a second pair of locations. The stimulation/sense electrodes 30 and 32 of the first GI tract lead 14 are preferably implanted against or through the serosa at the area within the transition of the corpus and the antrum on the great curvature and are employed for applying gastro-stimulation pulses to the stomach wall at these locations. Of course, other locations of the stimulation/sense electrodes 30 and 32 of the first GI tract lead 14 may be used, such as in the fundus 24, caudud corpus as well as the orad or terminal antrum 26. The stimulation/sense electrodes 34 and 36 of the second GI tract lead 16 are used to conduct any gastro-electrical signals traversing these locations of the stomach 22 to the IPG 12. Preferably the stimulation/sense electrodes 34 and 36 of the second GI tract lead 16 are positioned distally in the mid-antrum also along the great curvature, although these electrodes 34 and 36 may also be positioned in other locations.

The IPG 12 can comprise any of the hermetically enclosed IPGs disclosed in the above-listed patents that enclose a battery and an electrical operating system powered by a battery. Sense amplifiers of the IPG operating system sense the gastro-electrical signals conducted through the second set of electrodes 34 and 36, and pulse generator circuitry that generates electrical stimulation pulses that are conducted through the first set of electrodes 30 and 32 to the stomach 22 in accordance with a programmed operating mode and programmed operating parameter values. It will be understood that the stimulation/sense electrodes can all function as sensing and stimulation electrodes, and the selection of the stimulation/sense electrodes for sensing and stimulation functions can be programmed into the IPG 12.

Figure 2:
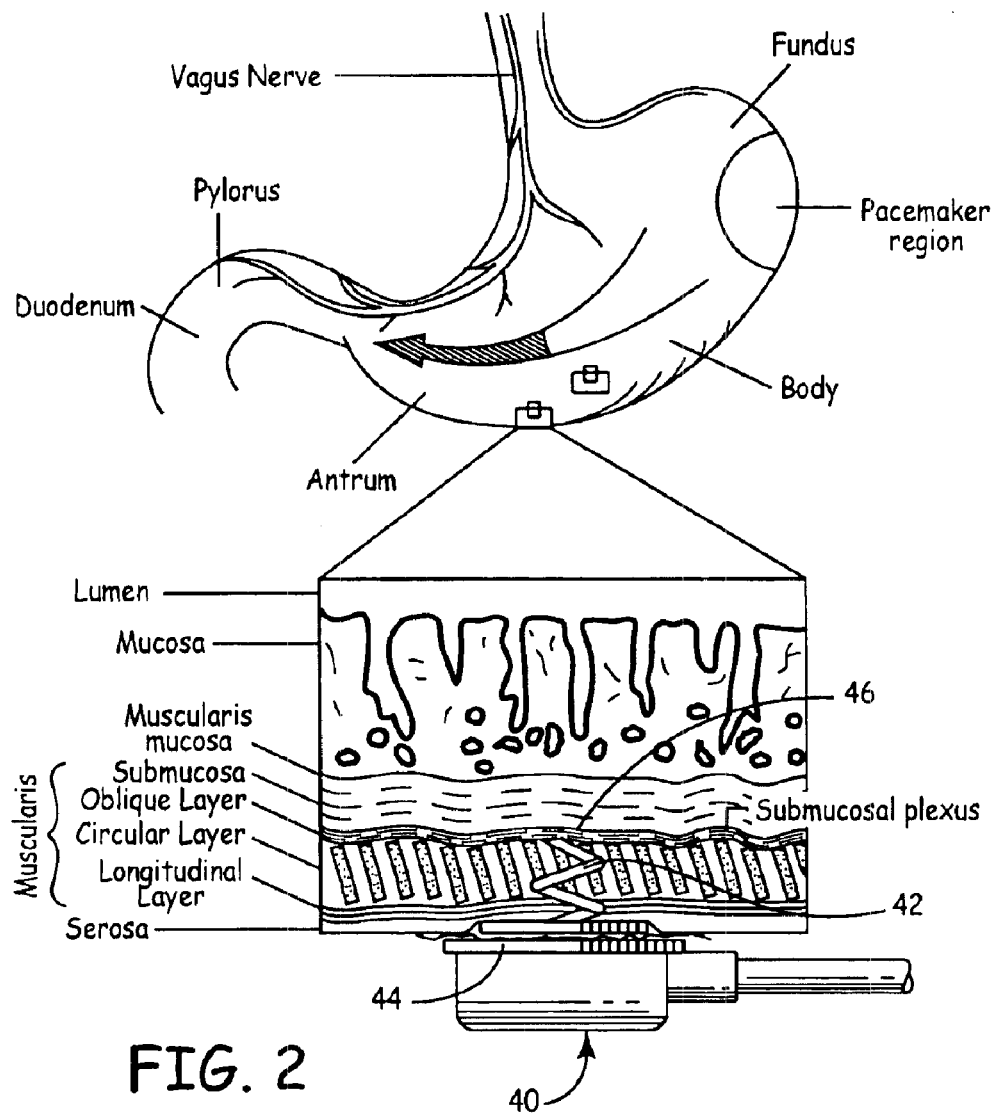
FIG. 2 is a detailed view of the stomach wall showing the affixation of an active fixation helix of a first screw-in electrode head within the muscularis externa.
Figure 6:
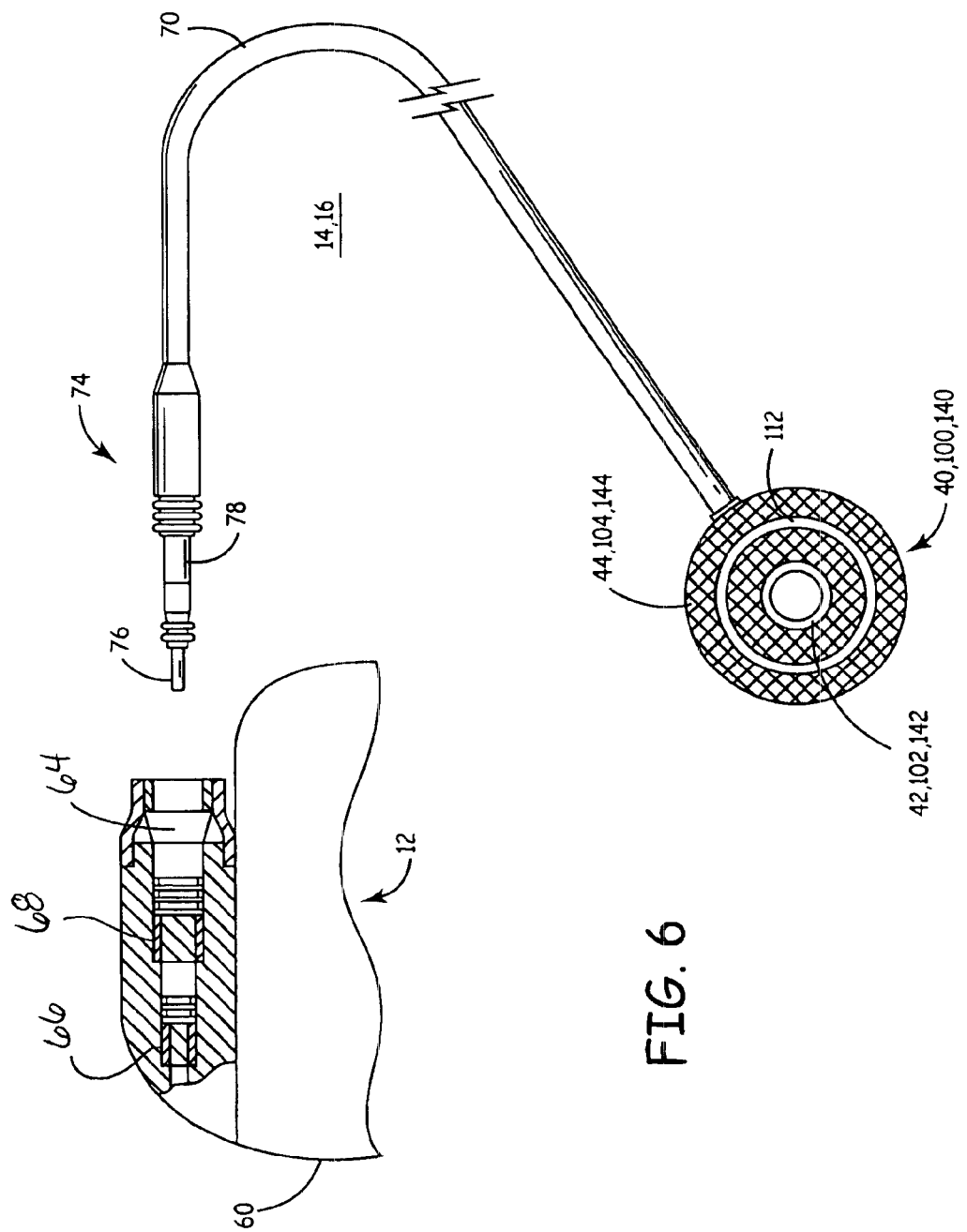
FIG. 6 is a further view of a unipolar or bipolar version of the first, second, and third GI tract screw-in leads of FIGS. 3, 4 and 5 depicting a plate mounted electrode spaced from the fixation helix.

The stomach wall of the stomach 22 comprises essentially seven layers of tissue that are shown in cross-section in FIGS. 2, 6, and 9. The seven tissue layers include the oblique, circular, and longitudinal muscle layers of the muscularis externa that contract and expand as described above, interposed between the interior stomach mucosa and the external serosa. In the preferred embodiments, the fixation mechanisms and electrodes of each lead perforate the serosa and lodge in the muscularis externa, particularly within the thickest circular layer as shown in FIGS. 2, 6, and 9. The active fixation mechanisms are selected from helixes and barbed hooks having sharpened tips or free ends that perforate the serosa and lodge in the muscularis externa or the submucosa. The maximal depth of penetration of any part of the fixation mechanism from the stop or plate is preferably in the range of 1 mm to 15 mm when the site comprises the antrum or in the range of 1 mm to 10 mm when the site comprises corpus or fundus to ensure that the free end does not extend substantially through the stomach wall.

Returning to FIG. 1, each of the stimulation/sense electrodes 30, 32, 34, 36 can be supported by distal electrode heads of unipolar or bipolar lead bodies of leads 14, 16. The active fixation mechanisms can either constitute a stimulation/sense electrode or can apply a separate stimulation/sense electrode against the serosa or within the muscularis externa. In bipolar GI tract lead embodiments, the active fixation mechanism comprises one stimulation/sense electrode and a separate stimulation/sense electrode is supported by the electrode head to bear against the serosa or within the muscularis externa. For convenience, the bipolar GI tract lead embodiments are described as follows, but it will be understood that second stimulation/sense electrode can be eliminated in unipolar GI tract embodiments of the invention. Of course, modern bipolar and unipolar GI tract leads have proximal in-line connector assemblies that fit into either unipolar or bipolar in-line connector sockets of GI tract IPGs so that they can be employed in respective unipolar and bipolar stimulation/sense modes.

Figure 3:
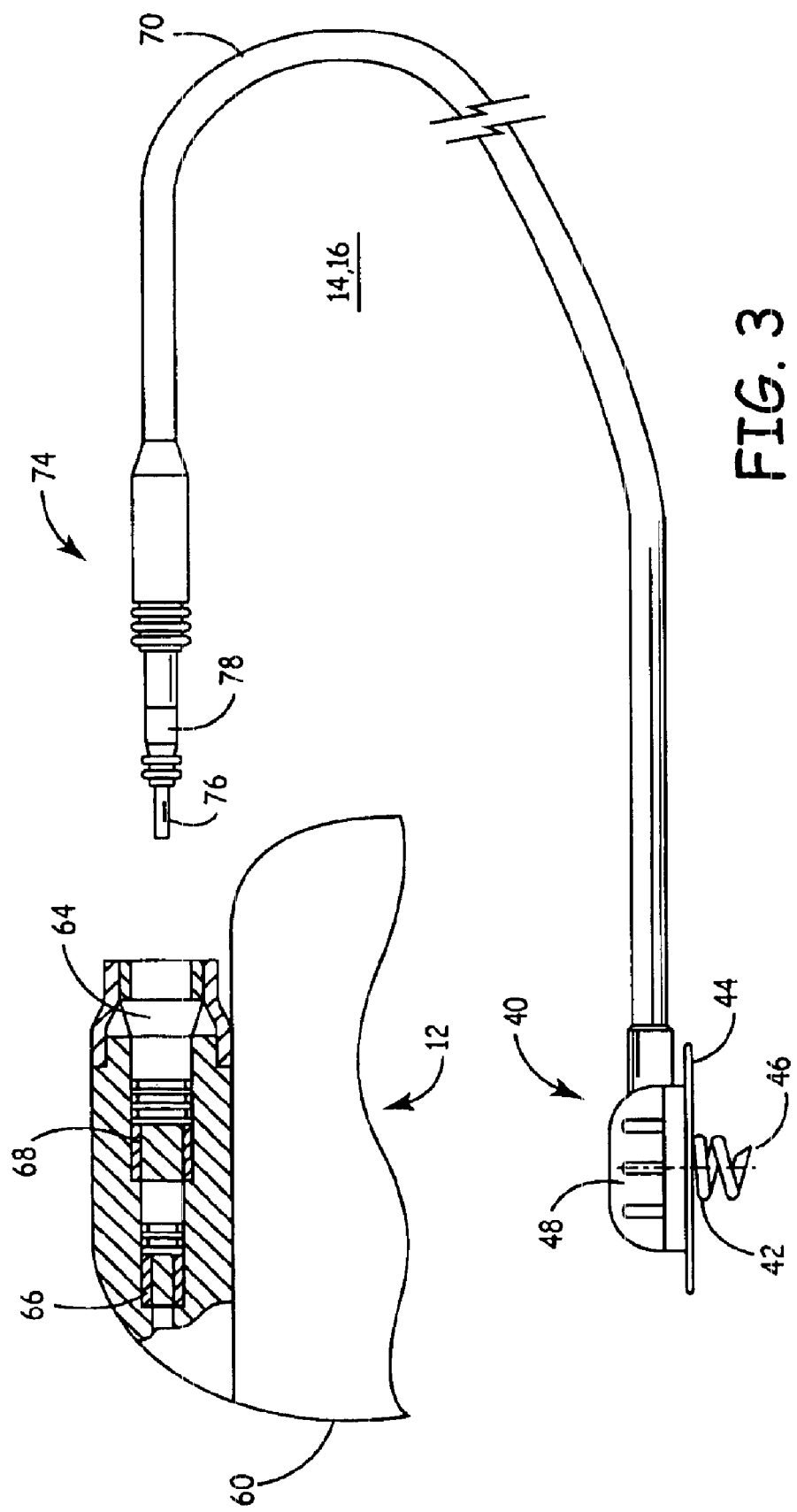
FIG. 3 is a side view of a first GI tract, unipolar or bipolar, screw-in lead of the type depicted in FIG. 2 having a single fixation helix that is fixed to the electrode head.

FIGS. 2 and 3 illustrate the preferred affixation of one type of fixation helix 42 of a screw-in electrode head 40 that can function as a stimulation/sense electrode in either a unipolar or bipolar GI tract lead embodiment or that can simply function as a fixation helix. The sharpened distal tip 46 and fixation helix 42 are advanced through the serosa and into the muscularis externa until the electrode head plate 44 abuts the serosa. The fixation helix 42 can be fixed to the plate 44 so that the entire electrode head must be grasped and rotated to screw the helix free end through the serosa and to the depicted depth of the muscularis externa in the manner of the electrode head described in the above-referenced '737 patent or '579 patent or '758 patent, for example. Or, the fixation helix 42 can be mounted to a rotatable mechanism inside the screw-in electrode head 40 that is rotated by a stylet as described in the above-referenced '946 patent or by rotation of the lead conductor as described in the above-referenced '006 patent. In this depiction, the lead body is shown extending proximally away from and parallel to the plate 44. However, it will be understood from the following that the lead body can extend away from screw-in electrode head 40 at any convenient angle or can be aligned at right angles to the plate 44 (that is, axially aligned with the helix axis) as shown in the embodiment of FIG. 4 described below.

In all cases, the fixation helix 42 extends away from the plate 44 of the screw-in electrode head 40 and is shaped to penetrate through the serosa and into the muscularis externa upon application of penetrating force through the electrode heads 40. The distal tip 46 can extend into the submucosa, but should not perforate the mucosa and enter the lumen. The plate 44 is drawn against the serosa and operatively contacts any stimulation/sense electrode located on the plate with the stomach wall. The plate 44 inhibits further advancement of the active fixation mechanism and perforation of the stomach wall, and the helix 42 cooperates with the plate 44 to inhibit dislodgement of the stimulation/sense electrode from operative contact with the stomach wall.

The IPG 12 further comprises a hermetically sealed housing 60 enclosing the battery and electrical operating system and a connector header 62 shown in partial cross-section in FIG. 3. A pair of bipolar connector sockets 64, 64' are formed in the connector header 62, each connector socket 64, 64' including IPG connector elements 66 and 68 that are electrically connected to circuitry within housing 60 through hermetically sealed feedthroughs in a manner well known in the art. Each bipolar connector socket 64, 64' receives a bipolar or unipolar lead connector assembly, e.g. depicted bipolar lead connector assembly 74, so that electrical connections are made between lead connector elements 76 and 78 and IPG connector elements 66 and 68, respectively, in a manner well known in the art.

Figure 4:
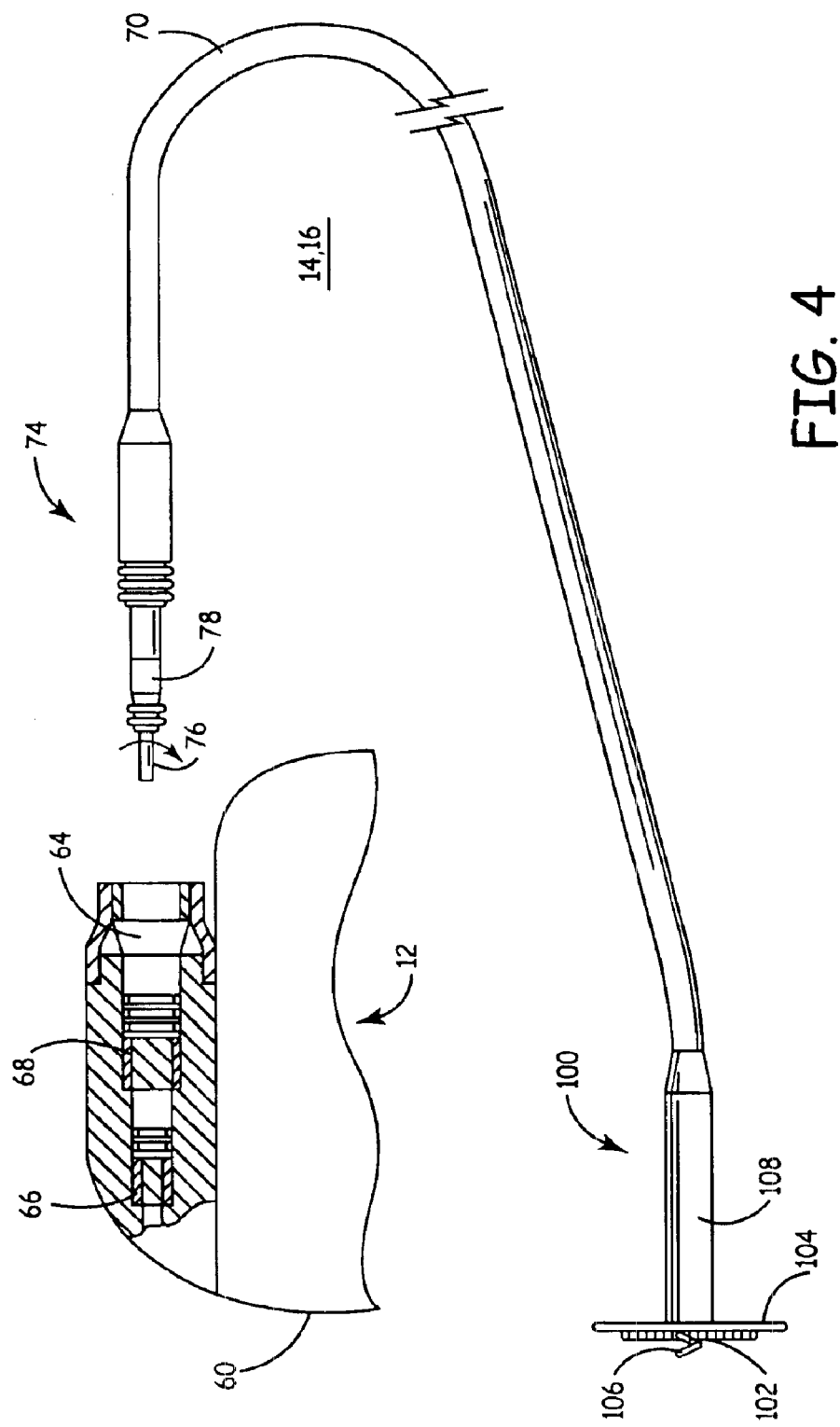
FIG. 4 is a side view of a second GI tract, unipolar or bipolar, screw-in lead having a single fixation helix that is rotatable with respect to the electrode head.

Another bipolar embodiment of the GI tract leads 14 and 16 is depicted in FIG. 4 employing an axially aligned screw-in electrode head 100 supporting a helix 102 extending in axial alignment with the lead body 70. In this embodiment of GI tract leads 14, 16, an inner, coiled wire conductor extends through a lead lumen extending from pin connector element 76 through the lead body 70 to the screw-in electrode head 100. The distal end of the coiled wire conductor is attached to the fixed end of the rotatable helix 102 within screw-in electrode head 100. The pin connector element 76 is rotatable with respect to the proximal connector assembly 74 to impart rotation torque through the lead conductor to rotate the helix 102 out of or back into the screw-in electrode head 100 in the manner described in the above-referenced '006 patent. The electrode head side 108 is grasped by an insertion tool to direct the electrode head plate 104 toward or against the serosa at the desired implantation site. The pin connector element 76 is rotated while the rotatable electrode head 100 is held steady to rotate the tip 106 and helix 102 to thereby screw them into the muscularis externa until the electrode head plate 104 engages against the serosa. The rotatable helix 102 can either be fully exposed or can be encased within the rotatable screw-in electrode head 100 and advanced from it during rotation of the pin connector element 76.

Figure 5:
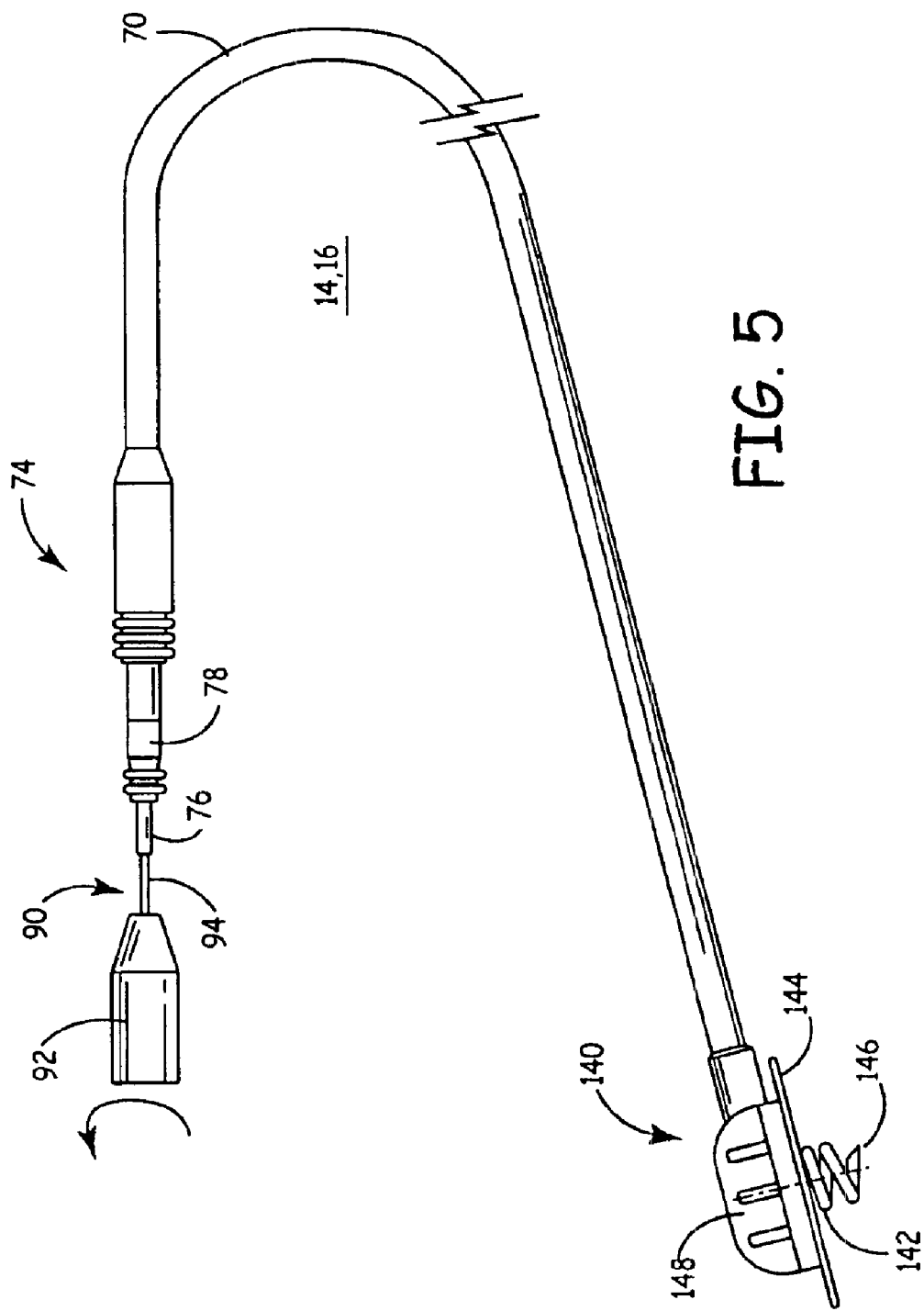
FIG. 5 is a side view of a third GI tract, unipolar or bipolar, screw-in lead having a single fixation helix that is rotatable with respect to the electrode head.

Another bipolar embodiment of the GI tract leads 14 and 16 is depicted in FIG. 5 employing a stylet 90 to rotate a rotatable fixation helix 142. The lead body 70 encloses a stylet lumen extending axially from a proximal lumen end opening in the pin connector element 76 through the lead body and to a rotatable screw-in electrode head 140. The rotatable screw-in electrode head 140 encloses a screw rotation mechanism that is attached to fixed end of the rotatable helix 142 and is of the type disclosed in the above-referenced '946 patent. An elongated stylet wire 94 of stylet 90 is inserted into the stylet lumen so that the stylet wire distal end engages the screw rotation mechanism. The electrode head sides 148 are grasped by an insertion tool to direct the electrode head plate 144 toward or against the serosa at the desired implantation site. The stylet handle 92 is rotated as the electrode head 140 is held steady so that the stylet wire 94 rotates the helix 142 and screws it's sharpened tip 146 into the muscularis externa until the plate 144 abuts the serosa. The rotatable helix 142 can either be fully exposed or can be encased within the rotatable screw-in electrode head 140 and advanced from it during rotation by the stylet 90.

As noted above, the electrode heads 40, 100, 140 can support unipolar or bipolar stimulation/sense electrodes, and the fixation helix 42, 102, 142 can also be a stimulation/ sense electrode. In the depicted bipolar lead embodiment of FIG. 3, the fixation helix 102 functions as a stimulation/sense electrode because it is electrically connected with the pin connector element 76. An exemplary embodiment of a second stimulation/sense electrode 112 is depicted in FIG. 6 as a conductive ring supported on plate 44, 104, 144 that is electrically connected through a second lead conductor within lead body 70 to a ring connector element 78. Alternatively, it will be understood that FIG. 5 also depicts a unipolar GI tract lead, wherein the helix 42, 102, 142 operates simply as a fixation mechanism and stimulation/sensing is conducted employing the ring-shaped stimulation/sense electrode 112 in conjunction with another GI tract lead stimulation/sense electrode or the conductive housing 60.

Figure 7:
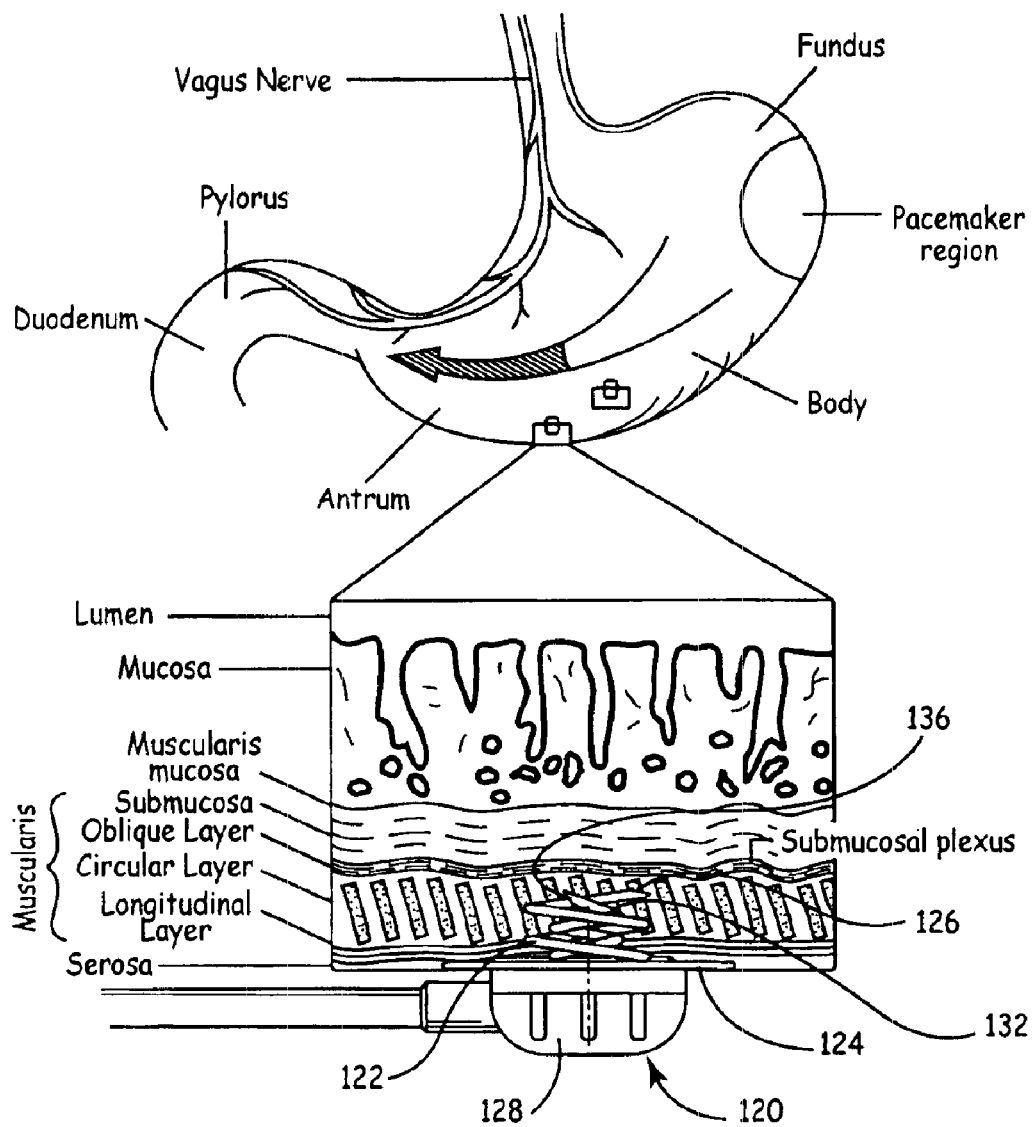
FIG. 7 is a detailed view of the stomach wall showing the affixation of dual active fixation helixes of a first screw-in electrode head within the muscularis externa.
Figure 8:
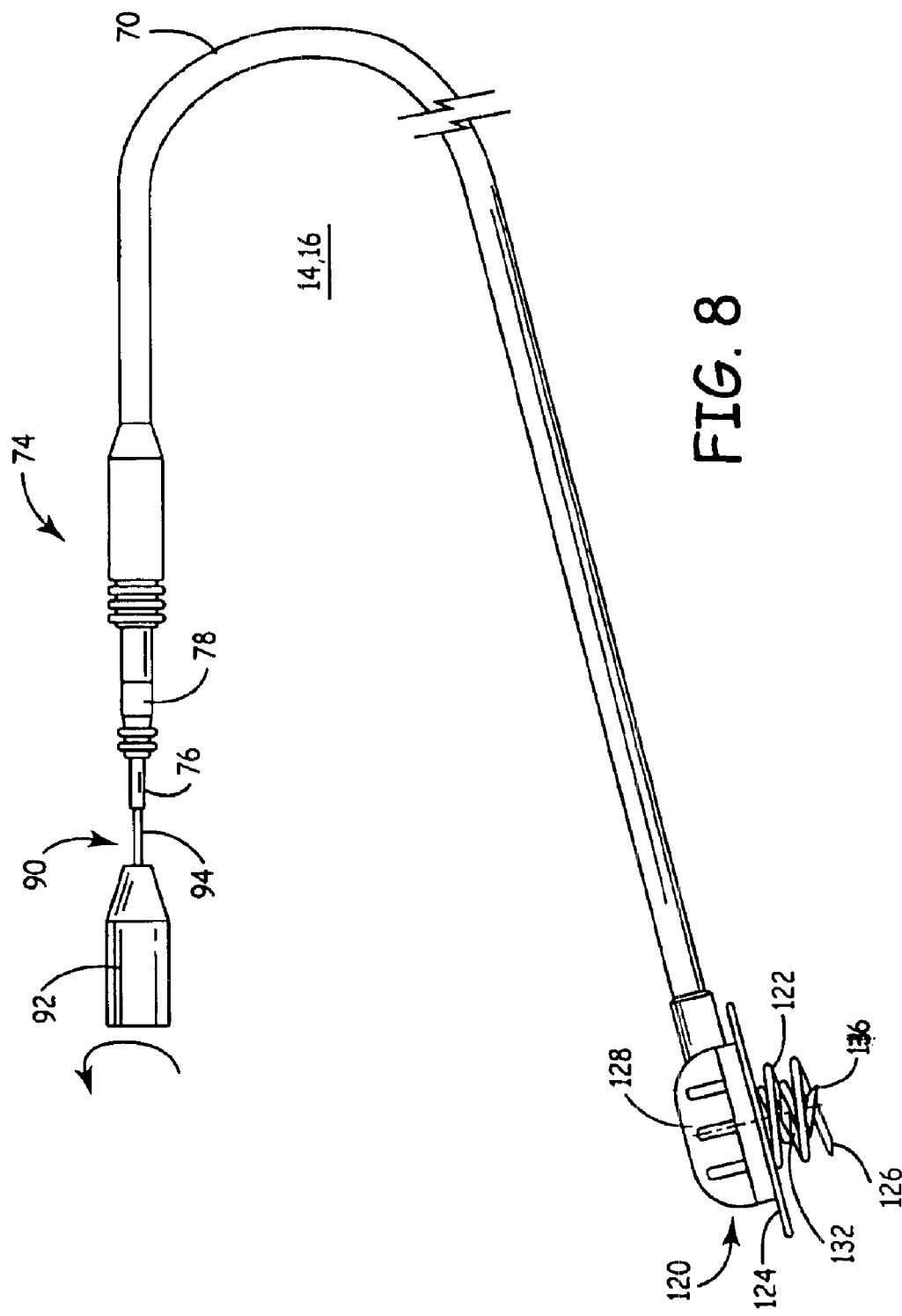
FIG. 8 is a plan side view of the unipolar or bipolar, dual helix screw-in lead of the type depicted in FIG. 7 wherein the fixation helixes are rotatable by a stylet to simultaneously screw the helixes into the muscularis externa.

FIGS. 7–9 illustrate a further exemplary embodiment of GI tract lead 14, 16 of the present invention having a lead body 70 extending between proximal connector assembly 74 and a dual helix electrode head 120. In this embodiment, an outer fixation helix 122 and an inner fixation helix 132 extend in co-axial relation away from electrode head plate 124 to sharpened tip helix free ends 126 and 136, respectively. The outer and inner fixation helixes 122 and 132 are attached at their fixed ends to outer and inner nested drive cylinders 130 and 134, respectively.

Again, the lead body 70 encloses a stylet lumen extending axially from a proximal lumen end opening in the pin connector element 76 through the lead body and to the rotatable screw-in electrode head 120. The rotatable screw-in electrode head 120 encloses the screw rotation mechanism comprising the nested drive cylinders 130 and 134 that are attached to fixed ends of the outer and inner rotatable helixes 122 and 132. The elongated stylet wire 94 of stylet 90 is inserted into the stylet lumen so that the stylet wire distal end engages the screw rotation mechanism. The electrode head sides 128 are grasped by an insertion tool to direct the electrode head plate 124 toward or against the serosa at the desired implantation site. The stylet handle 92 is rotated as the electrode head 120 is held steady so that the stylet wire 94 rotates the helixes 122 and 132 and screws their sharpened tips 126 and 136 into the muscularis externa until the plate 124 abuts the serosa. The rotatable helixes 122 and 132 can either be fully exposed or can be encased within the rotatable screw-in electrode head 120 and advanced from it during rotation by the stylet 90.

Figure 10:
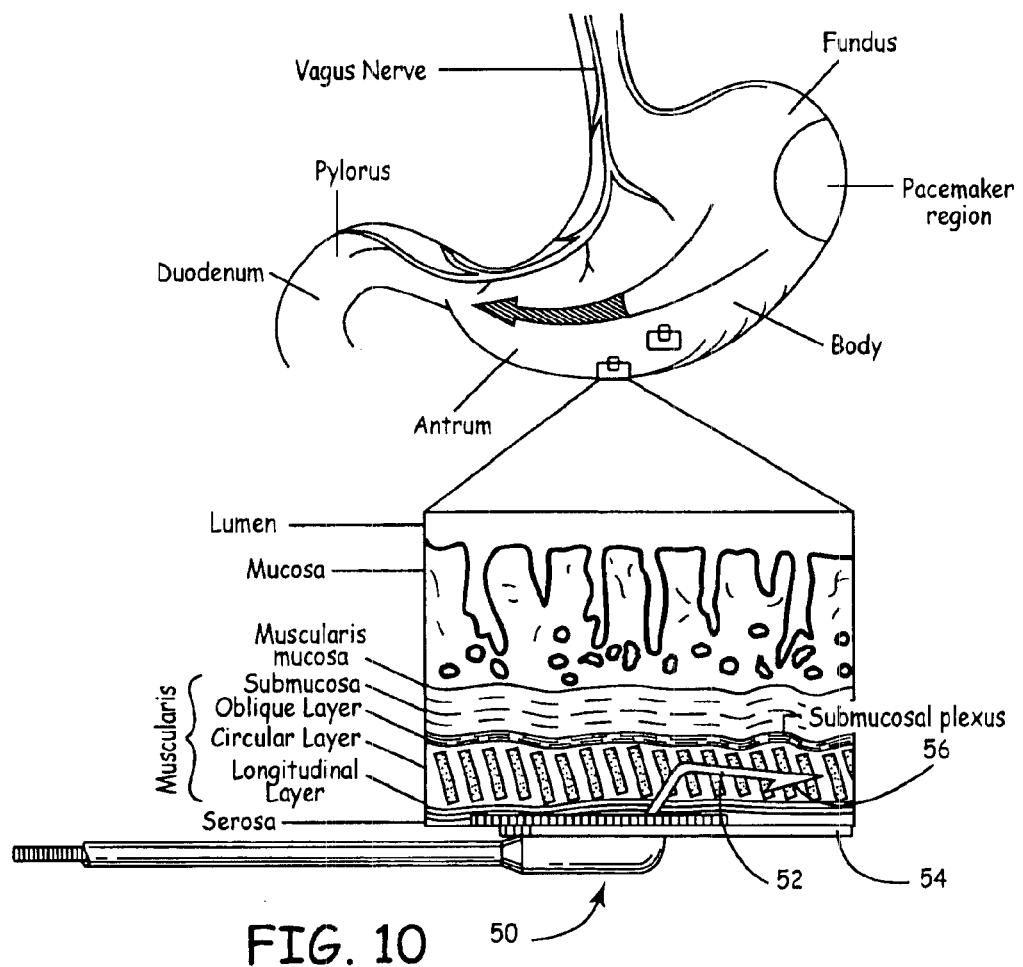
FIG. 10 is a detailed view of the stomach wall showing the affixation of an active fixation hook extending from a hook electrode head into the muscularis externa.
Figure 11:
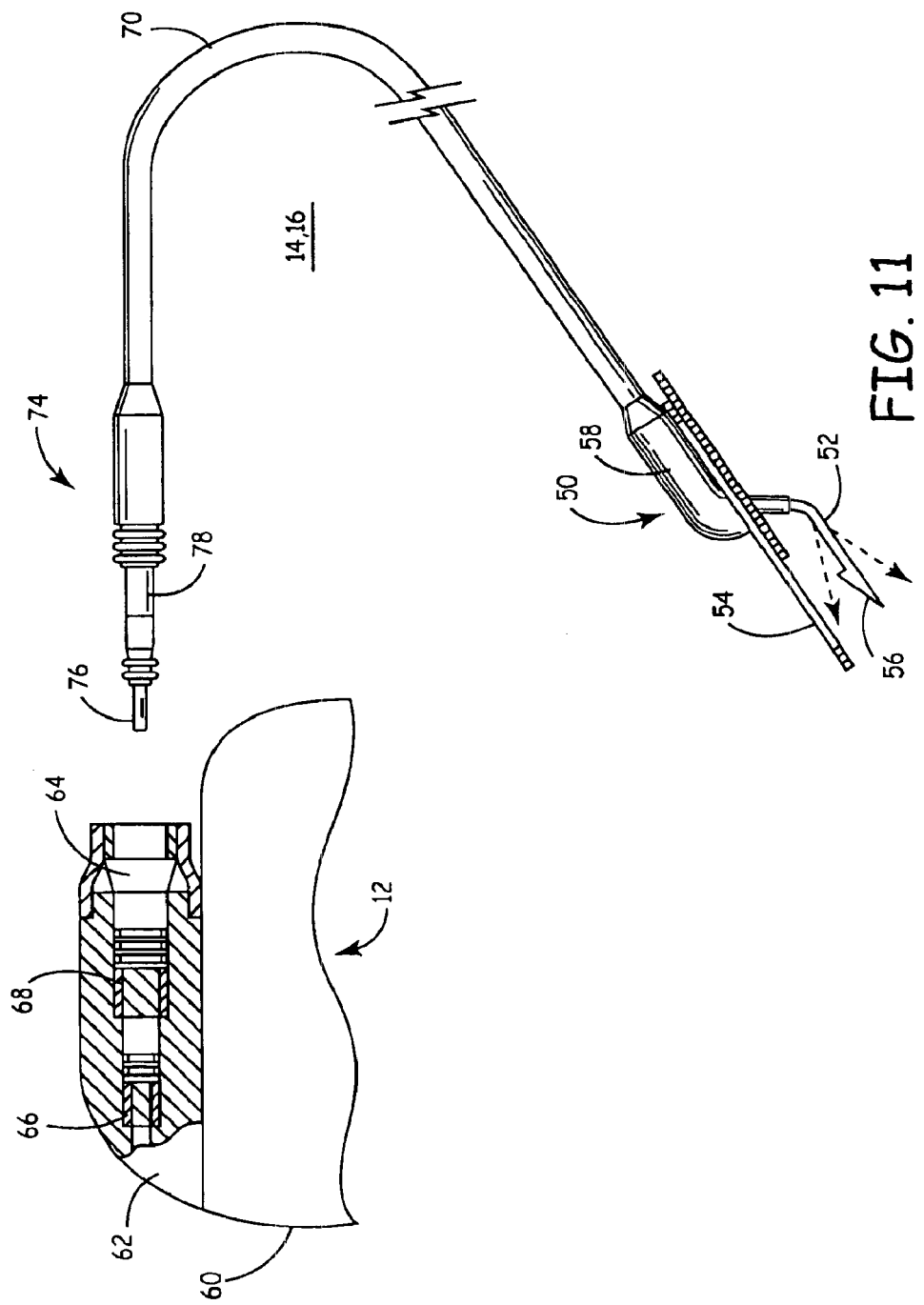
FIG. 11 is a plan side view of the unipolar or bipolar, GI tract lead of the type depicted in FIG. 10.
Figure 12:
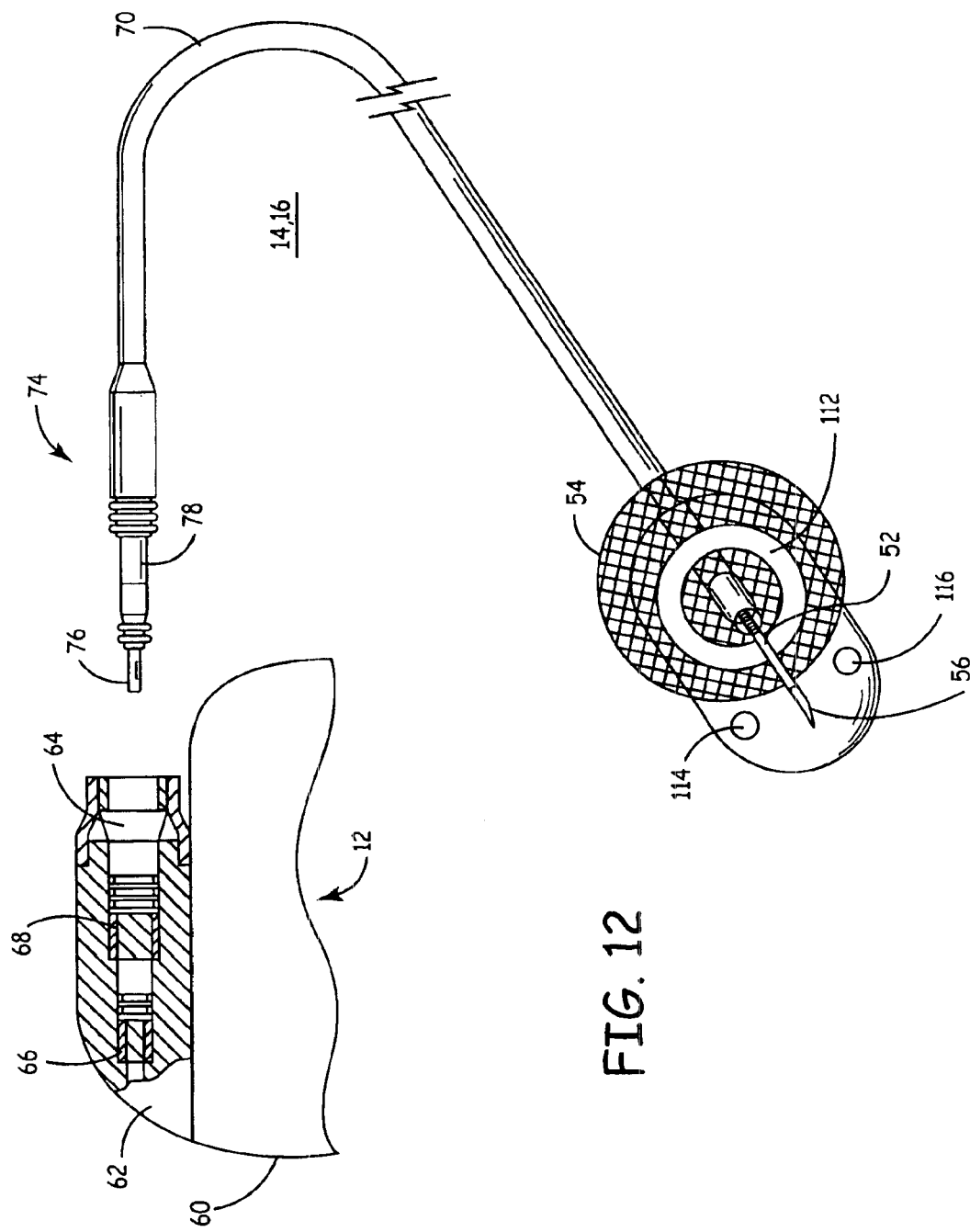
FIG. 12 is a further view of a bipolar version of the GI tract lead of the type depicted in FIG. 10 depicting a plate-mounted electrode spaced from the fixation hook.

FIGS. 10–12 depict a further embodiment of the active fixation GI tract leads 14, 16 of the present invention wherein affixation is effected by a barbed hook 52 extending away from hook plate 54 of hook electrode head 50. The barbed hook 52 comprises a hook shank having a proximal shank portion that extends from the hook fixed end away from the hook plate 54 to an elbow joining a distal shank portion that extends generally in parallel with the hook plate 54 to the barbed tip 56. The bend can be selected to extend the proximal shank portion and barbed tip 56 toward or away from the hook plate 54 as shown in broken lines in FIG. 11. The shank portion can be insulated as also shown in FIG. 11.

The barbed fixation hook 52 can either be a fixation mechanism alone in unipolar GI tract lead embodiments of the invention or can be coupled to an electrical conductor of lead body 70 extending to the pin connector element 76 in either unipolar or bipolar GI tract lead embodiments of the invention. An exemplary embodiment of a second stimulation/sense electrode 112 is depicted in FIG. 12 as a conductive ring supported on plate 54 that is electrically connected through a second lead conductor within lead body 70 to a ring connector element 78. Alternatively, it will be understood that FIG. 12 also depicts a unipolar GI tract lead, wherein the hook 52 operates simply as a fixation mechanism and stimulation/sensing is conducted employing the ring-shaped stimulation/sense electrode 112 in conjunction with another GI tract lead stimulation/sense electrode or the conductive housing 60.

FIG. 10 illustrates the preferred affixation of fixation hook 52 pressed through the serosa and into the muscularis externa until the electrode head plate 54 abuts the serosa. The fixation hook and electrode 52 can be pressed through the serosa and into the muscularis externa employing a forceps grasping the electrode head 50 or a tool of the type disclosed in the above-referenced '818 patent. During such implantation, the opposed head sides 58 of the hook electrode head 50 are grasped by forceps or the first hook electrode head 50 is grasped by a tool of the type described in the above-referenced '818 patent. The tool is used to advance the hook electrode head 50 to the site of the stomach or other site of the GI tract and to press the hook tip 56 through the serosa until the plate 54 is seated against the serosa. The grasp exerted by the forceps or tool is then released.

It should be understood that the shape of the hook 52 can be altered in many ways, and that the hook plate can support more than one such hook having hook shanks that extend in parallel to one another or toward one another in the manner of the hooks disclosed in the above-referenced '818 patent.

The plate-mounted stimulation/sense electrode 112 is spaced from the helixes or hooks of the various embodiments and can have any shape and surface area. Moreover, the second stimulation/sense electrode 112 can be surface mounted to the electrode head plate, recessed within the plate surface or protruding away from the plate surface so as to extend against the serosa. The second stimulation/sense electrode 112 can also be formed of one or more conductive pin having a sharpened tip and a length enabling perforation of the serosa and lodging substantially within the muscularis externa.

The fixation hooks or helixes functioning as stimulation/sense electrodes can be formed of bio-compatible conductive materials that are exposed entirely or selectively insulated in portions thereof embedded in the muscularis externa. The plate electrode 112 can also be formed of bio-compatible conductive materials. In all cases, the stimulation/sense electrode surface can be coated with a porous platinized structure to reduce polarization and/or an anti-inflammatory agent that inhibits inflammation that can negatively affect the ability to sense electrical signals of the GI tract or to efficiently deliver electrical stimulation. The anti-inflammatory agents can be embedded into an MCRD carried by the electrode head, particularly in the surface of the plates 44 and 54. Such anti-inflammatory agents include steroids, anti-bacterial agents, baclofen, dexamethasone sodium phosphate and beclomethasone phosphate.

The electrode head plates 44, 54, 104, 124, 144 can comprise a fabric mesh disc of DACRON or other biocompatible material or a silicone rubber disc or a combination of both that is flexible, biocompatible, and encourages tissue growth adhesion with the serosa of the GI tract wall. The plates 44, 54, 104, 124, 144 can be substantially planar when unrestrained as depicted in the figures or may have any other convenient curvilinear shape that operates as a stop. In addition, once the attachment is made, it is possible to reinforce the attachment by suturing the plates 44, 54, 104, 124, 144 to the stomach wall, placing the sutures either through the flexible plate or preformed suture holes in the plates 44, 54, 104, 124, 144. Such suture holes 114, 116 through plate 54 are shown in FIG. 12, for example, While above described embodiments comprise GI tract leads that fit within bipolar IPG connector assemblies, it will be understood that the present invention can be applied to any multi-polar IPG connector assemblies.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of GI tract neurostimulators are not disclosed and are not necessary to the practice of the present invention. In addition, it will be understood that specifically described structures, functions and operations set forth in the above-referenced patents can be practiced in conjunction with the present invention, but they are not essential to its practice.

Thus, embodiments of the IMPLANTABLE GASTROINTESTINAL LEAD WITH ACTIVE FIXATION are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A gastrointestinal lead adapted to be implanted within the body at a site of the GI tract to conduct electrical stimulation from an implantable or external gastrointestinal stimulator to the site and to conduct electrical signals of the GI tract from the site to the implantable or external gastrointestinal stimulator comprising:

an elongated lead body extending from a lead body proximal end to a lead body distal end;

an electrode head formed at the lead body distal end having a plate adapted to bear against the serosa, the electrode head supporting a first stimulation/sense electrode;

a first lead connector element at the lead body proximal end;

a first lead conductor enclosed within the lead body and electrically coupled to the first stimulation/sense electrode and the first lead connector element; and an active fixation mechanism extending away from the plate of the electrode head shaped to penetrate through the serosa and into the muscularis externa upon application of force to the electrode head to draw the plate against the serosa and operatively contact the first stimulation/sense electrode with the GI tract wall, whereupon the plate inhibits further advancement of the active fixation mechanism and perforation of the GI tract wall and the active fixation mechanism inhibits dislodgement of the first stimulation/sense electrode from operative contact with the GI tract wall, wherein:

the active fixation mechanism comprises an inner helix and an outer helix, the inner helix comprising one or more coil turns extending from an inner helix fixed end and an inner helix free end adapted to penetrate through the serosa, and the outer helix comprising one or more coil turns extending from an outer helix fixed end and an outer helix free end adapted to penetrate through the serosa; and further comprising:

means for supporting the inner and outer helixes in co-axial relation extending away from the electrode plate means for rotating the inner and outer helixes to advance the inner and outer helixes into the muscularis externa until the plate is drawn against the serosa.

2. The gastrointestinal lead of claim 1, wherein the inner and outer helixes have an axial length enabling a depth of penetration from the plate in the range of 1 mm to 15 mm when the site comprises the antrum of the stomach wall or in the range of 1 mm to 10 mm when the site comprises corpus or fundus of the stomach wall to ensure that the inner and outer helix free ends do not extend substantially through the stomach wall.

3. The gastrointestinal lead of claim 1, wherein:

the inner helix free end is electrically connected with the first lead conductor to function as the first stimulation/sense electrode; and further comprising:

a second lead connector element at the lead body proximal end; and a second lead conductor enclosed within the lead body and electrically coupled to the outer helix free end to function as a second stimulation/sense electrode.

4. The gastrointestinal lead of claim 1, wherein:

the elongated lead body encloses a stylet lumen extending into the electrode head; and the rotating means comprises a rotatable mechanism fitted into the electrode head and attached to the inner and outer helix fixed ends to extend the inner and outer helixes orthogonally to the plate, the rotatable mechanism adapted to be engaged by a stylet advanced through the stylet lumen, whereby the rotatable mechanism is rotated by the stylet to rotate the inner and outer helixes and advance the inner and outer helix free ends through the serosa and into the muscularis externa until the plate is drawn against the serosa.

5. A method of stimulating a site of the GI tract with electrical stimulation from an implantable or external gastrointestinal stimulutor and of conducting electrical signals of the GI tract from the site to the implantable or external gastrointestinal stimulator comprising:

surgically accessing the serosa of the GI tract at the site to locate an electrode head of a medical electrical lead oriented to the serosa, the medical electrical lead extending between a connector at a lead body proximal end to an electrode head at a lead body distal end, the electrode head supporting a first electrode and an active fixation mechanism extending from a plate;

perforating the serosa with the active fixation mechanism of the electrode head: advancing the active fixation mechanism into the muscularis externa to apply the first electrode into operative relation with the GI tract wall and until the plate bears against the serosa to inhibit further advancement of the active fixation means and perforation of the GI tract wall; and connecting the connector at the lead body proximal end with an implantable or external stimulator to enable conduction of electrical signals through a lead conductor enclosed within the lead body and electrically coupled to the first stimulation/sense electrode and the connector, whereby the active fixation mechanism inhibits dislodgement of the first stimulation/sense electrode from operative relation with the GI tract wall wherein:

the elongated lead body encloses a stylet lumen;

the electrode head comprises:

a first helix comprising one or more coil turns extending from a helix fixed end and a helix free end and having a first helix axis;

a second helix comprising one or more coil turns extending from a helix fixed end and a helix free end and having a second helix axis co-axially aligned with the first helix axis;

a rotatable mechanism fitted into the electrode head and attached to the first and second helix fixed ends to extend the helix axes orthogonally to the plate;

the perforating step comprises penetrating the serosa with the first and second helix free ends; and the advancing step comprises inserting a stylet into the stylet lumen to engage the rotatable mechanism and rotating the stylet to rotate the first and second helixes to advance each coil turn into the muscularis externa until the plate is drawn against the serosa.

6. A system providing gastrointestinal sensing and/or stimulation comprising:

a gastrointestinal lead comprising an elongated gastrointestinal lead body comprising:

an elongated lead body extending from a lead body proximal end to a lead body distal end;

an electrode head formed at the lead body distal end having a plate adapted to bear against the serosa, the electrode head supporting a first stimulation/sense electrode;

a first lead connector element at the lead body proximal end;

a first lead conductor enclosed within the lead body and electrically coupled to the first stimulation/sense electrode and the first lead connector element; and an active fixation mechanism extending away from the plate of the electrode head shaped to penetrate through the serosa and into the muscularis externa upon application of force to the electrode head to draw the plate against the serosa and operatively contact the first stimulation/sense electrode with the GI tract wall, whereupon the plate inhibits further advancement of the active fixation mechanism and perforation of the GI tract wall and the active fixation mechanism inhibits dislodgement of the first stimulation/sense electrode from operative contact with the GI tract wall, the active fixation mechanism comprising an inner helix and an outer helix, the inner helix comprising one or more coil turns extending from an inner helix fixed end and an inner helix free end adapted to penetrate through the serosa, and the outer helix comprising one or more coil turns extending from an outer helix fixed end and an outer helix free end adapted to penetrate through the serosa; and further comprising:

means for supporting the inner and outer helixes in co-axial relation extending away from the electrode plate, means for rotating the inner and outer helixes to advance the inner and outer helixes into the muscularis externa until the plate is drawn against the serosa;

deploying means for deploying the active fixation mechanism extending away from the plate of the electrode head and penetrating through the serosa and into the muscularis externa to draw the plate against the serosa and operatively contact the stimulation/sense electrode with the GI tract wall, whereby the plate inhibits further advancement of the active fixation mechanism and perforation of the GI tract wall, and the active fixation mechanism inhibits dislodgement of the stimulation/sense electrode from operative contact with the GI tract wall; and an implantable or external gastrointestinal stimulator having a gastrointestinal stimulator connector coupled with the lead connector assembly to conduct electrical stimulation from the implantable or external gastrointestinal stimulator between the first and second sites of the GI tract and to conduct electrical signals of the GI tract from the first and second sites to the implantable or external gastrointestinal stimulator.

7. The system of claim 6, wherein the inner and outer helixes have an axial length enabling a depth of penetration from the plate in the range of 1 mm to 15 mm when the site comprises the antrum of the stomach wall or in the range of 1 mm to 10 mm when the site comprises corpus or fundus of the stomach wall to ensure that the inner and outer helix free ends do not extend substantially through the stomach wall.

8. The system of claim 6, wherein:

the inner helix free end is electrically connected with the first lead conductor to function as the first stimulation/sense electrode; and further comprising:

a second lead connector element at the lead body proximal end; and a second lead conductor enclosed within the lead body and electrically coupled to the outer helix free end to function as a second stimulation/sense electrode.

9. The system of claim 6, wherein:

the elongated lead body encloses a stylet lumen extending into the electrode head; and the rotating means comprises a rotatable mechanism fitted into the electrode head and attached to the inner and outer helix fixed ends to extend the inner and outer helixes orthogonally to the plate, the rotatable mechanism adapted to be engaged by a stylet advanced through the stylet lumen, whereby the rotatable mechanism is rotated by the stylet to rotate the inner and outer helixes and advance the inner and outer helix free ends through the serosa arid into the muscularis externa until the plate is drawn against the serosa.

* * * * *